(12) United States Patent
Thompson et al.

(10) Patent No.: US 11,253,894 B1
(45) Date of Patent: Feb. 22, 2022

(54) WASTE DESTRUCTION DEVICE

(71) Applicants: Robert Thompson, Laguna Woods, CA (US); James Slanina, Tampa, FL (US)

(72) Inventors: Robert Thompson, Laguna Woods, CA (US); James Slanina, Tampa, FL (US)

(73) Assignee: Safe Dispose LLC, Tampa, FL (US)

( * ) Notice: Subject to any disclaimer, the term of this patent is extended or adjusted under 35 U.S.C. 154(b) by 0 days.

(21) Appl. No.: 15/929,738

(22) Filed: May 19, 2020

Related U.S. Application Data

(63) Continuation of application No. 16/459,037, filed on Jul. 1, 2019, now Pat. No. 10,688,543.

(60) Provisional application No. 62/692,691, filed on Jun. 30, 2018.

(51) Int. Cl.
| | |
|---|---|
| *B09B 3/00* | (2006.01) |
| *A61L 11/00* | (2006.01) |
| *A62D 3/19* | (2007.01) |
| *B01D 53/34* | (2006.01) |
| *A61L 2/00* | (2006.01) |

(52) U.S. Cl.
CPC ............ *B09B 3/0075* (2013.01); *A61L 11/00* (2013.01); *B09B 3/0083* (2013.01); *A61L 2/0023* (2013.01); *A62D 3/19* (2013.01); *B01D 53/34* (2013.01)

(58) Field of Classification Search
CPC ....... B09B 3/00; B09B 3/0075; B09B 3/0083; A61L 11/00; A61L 2/0023; A62D 3/19; B01D 53/34
USPC ........................................................... 241/65
See application file for complete search history.

(56) References Cited

U.S. PATENT DOCUMENTS

2017/0253891 A1\* 9/2017 Gitschel .................... B09B 3/00

\* cited by examiner

*Primary Examiner* — Edward M Johnson
(74) *Attorney, Agent, or Firm* — Nicholas Pfeifer; Smith & Hopen, P. A.

(57) ABSTRACT

A device for converting harmful waste products into environmentally friendly discharge is provided. The discharge, as a result of the waste destruction process, meets or exceeds the Environmental Protection Agency (EPA) standards. The device includes a waste disposal chamber where a crucible is positioned. The crucible is configured to retain a removable basket that is heated via induction heating. The waste residing within the removable basket is then vaporized and ionized within a vacuum to form a waste gas that is drawn through an accelerated jet of thermal plasma via vacuum suction. Once the waste gas passes through the plasma, it passes through a discharge duct where it is condensed by a heat exchanger and exhausted into the environment surrounding the device.

15 Claims, 4 Drawing Sheets

WASTE DESTRUCTION DEVICE

CROSS-REFERENCE TO RELATED APPLICATIONS

This nonprovisional application is a continuation of and claims priority to nonprovisional application Ser. No. 16/459,037, entitled "A DEVICE FOR THE DESTRUCTION OF BIOHAZARDOUS WASTE AND METHOD OF USE," filed Jul. 1, 2019 by the same inventor(s), now allowed, which is a continuation of and claims priority to provisional application No. 62/692,691, entitled "Pyrolysis/Plasma Arc Waste Destruction," filed Jun. 30, 2018 by the same inventor(s).

BACKGROUND OF THE INVENTION

1. Field of the Invention

This invention relates, generally, to the field of on-site or mobile treatment of waste, including infectious, medical, biological, pathological, pharmaceutical, *cannabis*, and chemotherapy waste. More specifically, it relates to the process of thermochemical decomposition of organic material at elevated temperatures in the absence of oxygen (or any halogen) in a single chamber with an output air quality that meets or exceeds the Environment Protection Agency (EPA) regulations.

2. Brief Description of the Prior Art

This invention relates to the pyrolytic destruction of materials that require an incineration type process to comply with Federal and State laws. This classification of material must be managed and disposed of effectively.

Various methods have been tried for disposing of toxic wastes, including thermal destruction, chemical detoxification, long term encapsulation, and specific landfills methods. With the exception of high-temperature incineration, little success has been demonstrated for the safe disposal of highly toxic or extremely persistent wastes, such as polychlorinated biphenyl's (PCB). Further, very few of the disposal methods tried to date have been able to be developed to operate on a commercial scale because it generally has not been possible to demonstrate to the various regulatory agencies that the disposal methods used in the past have been completely safe. Demonstrations have shown that the plasma arc is capable of atomizing and ionizing toxic organic compounds and that these atoms and ions recombine into simple products.

Of the many methods attempted for the disposal of toxic or hazardous waste, thermal destruction has been the most promising. Toxic materials are usually very stable organic molecules, and they require long dwell times at high temperatures to effect thermal destruction. Some combustion or incineration systems can achieve the necessary conditions, but the facilities required are very large, and often the discharge product of the combustion process presents as much of a disposal problem as the original toxic waste. Significant air treatment equipment on these facilities is required for operation. In addition, the waste must be transported to these large facilities as very few are permitted to operate in the United States. Other systems require separate chambers to capture the waste gas and treat the dioxin gas output with alkaline spray systems to neutralize the particulate matter. Water sources to help with the cool down process of the chamber.

For example, U.S. Pat. No. 8,870,735 B2 (735 Patent) to Fortunato Villamagna relates to a waste disposal system that converts waste products into benign and useful output using a stream of free radicals, such as those generated in a low energy or "cold" plasma to react with smoke. However, the system disclosed in the '735 Patent has significant drawbacks. For example, the '735 Patent uses cold plasma to break up smoke using free radicals, as opposed to hot plasma that is designed to burn the escaping gases and, in doing so, burn toxic chemicals, such as dioxins, from the escaping gases. With cold plasma techniques, various components of the mixture at various points along the secondary chamber are measure, and, based on the measured amounts, the input of smoke, air steam, and other input fluids is changed. This process requires sophisticated control systems, which could be susceptible to error if not monitored. The '735 Patent teaches that, for example, "if the smoke is generated using waste products from a hospital, the typical breakdown of hospital waste is used to determine the mixture of air, steam, inert gas, etc. into the secondary chamber." '735 Patent, 4:66-67; 5:1-3. This process assumes a certain standard mixture in hospital waste, as well as other wastes converted by the system, with the mixtures being calculated and different for various waste materials. Accordingly, the cold plasma technique described in the '735 Patent fails to provide a comprehensive and user-friendly solution to the efficient destruction of waste material.

Accordingly, what is needed is a waste destruction system for the destruction of harmful waste using an induction coil heating system to atomize and ionize the waste material and hot plasma to incinerate the toxic gases, such as dioxins that are produced. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a waste destruction device that disposes of waste by atomizing and ionizing a waste matter and converting it to a harmless gas and small amount of ash having a minimal effect on the environment is now met by a new, useful, and nonobvious invention.

The novel structure includes a waste destruction device that includes a removable basket that is disposed to receive a predetermined about of waste. The basket includes a plurality of apertures to facilitate the even distribution of heat within a crucible. The crucible is formed, having a crucible socket that is configured to receive the removable basket. An induction coil is in thermodynamic communication with and disposed around the outside surface of a crucible body. A waste disposal chamber includes a disposal body, a removable lid, and a coupling structure that couples the lid to the disposal body sealing in the waste disposal chamber and the crucible within. The disposal body forms an internal cavity that receives the crucible and further includes a thru-hole is in communication with the internal cavity. The induction coil uses electromagnetic induction to rapidly heat the removable basket to an operating temperature between 950° F. and 1400° F. that results in the atomizing and ionizing the waste disposed within the removable basket resulting in the formation of waste gas. In an embodiment, waste gas may include a syn gas (synthesis gas) consisting primarily of hydrogen, carbon monoxide, and carbon dioxide.

A first duct has a first end and a second opposite end. The first end is disposed through the thru-hole forming an airtight seal and allows the waste gas to flow from the waste disposal chamber to the catalytic converter, which is coupled at the second end. The catalytic converter includes a honeycomb structure with palladium, rhodium, and platinum is used to convert carbon monoxide and unburned hydrocarbons into carbon dioxide and water vapor. A second duct has a first end and a second opposite end. The first end is coupled to the catalytic converter such that the waste gas flows from the catalytic converter, through the second duct, and into the plasma chamber.

The plasma chamber includes a plasma head disposed within the plasma chamber and provides an accelerated jet of hot plasma. A discharge duct is connected to the plasma chamber such that when the waste gas flows from the second duct into the plasma chamber, the waste gas passes through the accelerated jet of hot plasma, incinerating harmful gages, and discharging the resulting non-toxic gages through a discharge duct. The discharge duct further includes a heat exchanger that rapidly cools the waste gas flowing within the discharge duct such that waste gas condenses into relatively safe and environmentally friendly gases, complying with environmental protection agency standards and regulations.

A third duct is also provided, having a first end a second opposite end. The first end is connected to the plasma chamber, and the second end is connected to a pressure altering pump. The pressure altering pump may be a compressor, a vacuum pump, or a combination of the two pumps in a single system. The compressor can be used to cool the crucible by forcing compressed air into the system such that cool air passes over the crucible, rapidly cooling it down.

An object of the invention includes a control panel that comprises a user interface device, a programmable logic controller, and a microprocessor. The user interface is disposed to receive user input such that the logic controller takes the user input and operates a microprocessor to send an electrical signal to the temperature sensor, humidity sensor, carbon dioxide sensor, and oxygen sensor. In an embodiment, the waste destruction device includes a carbon dioxide sensor that detects the level of carbon dioxide within the environment surrounding the waste destruction device. If the carbon dioxide levels exceed a safe operating level, the programmable logic controller will shut the waste destruction device down. The waste destruction device may include humidity and temperature sensors in electrical communication with the programmable logic controller to monitor the temperature and humidity levels within the crucible and automatically adjusts the parameters according to the programmed code. The crucible may include a safety gas sensor such that if a sufficient level of oxygen or other combustible gas is detected within the crucible, the programmable logic controller shuts the waste destruction device down. The programmable logic controller also controls an indicator light displaying the operating status of the waste destruction device.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The waste destruction device described herein converts waste material into safe and harmless byproducts using pyrolysis, a catalytic converter, and hot plasma. Pyrolysis is the process of rapidly heating material in the absence of oxygen, resulting in the decomposition of the organic material without combustion. The decomposition of these materials results in a variety of gases and a small amount of charcoal once the process is complete. The output generated by this waste destruction device, as described herein, produces an output that is environmentally friendly and in compliance with the Environmental Protection Agency (EPA) regulations along with regulatory bodies regulations.

The present invention provides a significant advantage over the previous system, such as those described in the '735 Patent, as the present invention does not require the adjustment of a mixture of smoke, air, steam, and inert gases to operate a cold plasma-based waste destruction device that reduces the risk of an operating error, harmful compounds resulting from improper operation, and the operating time of the system. Instead, the present waste destruction device simply requires the user to place waste within the chamber, set the temperature and time, and let the system run—no specific calculation of a "mixture" as required by the '735 Patent. The present invention will be discussed hereinbelow.

Figure 1:
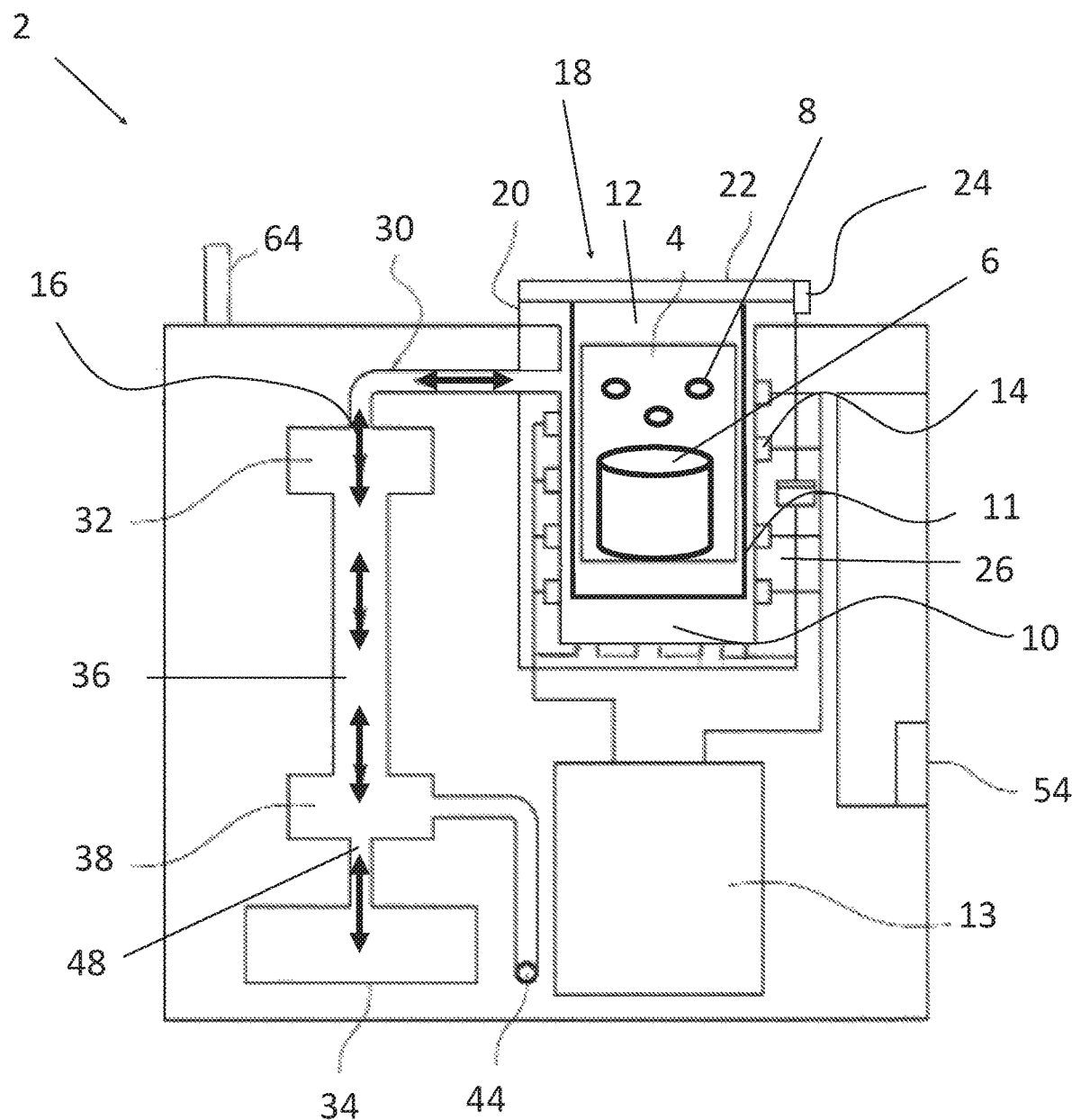
FIG. 1 is an orthogonal view of an embodiment of the waste destruction device, depicting the internal components of the device.

FIG. 1 depicts an embodiment of waste destruction device 2 used for the destruction of medical, household, industrial, office, and culinary waste among a plethora of other waste products. Waste destruction device 2 includes waste disposal chamber 18 comprising disposal body 20, removable lid 22, and coupling structure 24 for securing lid 22 to disposal body 20. Crucible 10, removable basket 4, and waste 6 are removably housed within internal cavity 26 of waste disposal chamber 18. In an embodiment, high-temperature insulation is disposed within the internal cavity 26 and resides between the disposal body 18 and crucible 10. In an embodiment, the insulation is fiberglass insulation, foam board insulation, mineral wood insulation, spray foam insulation, denim insulation, or any other insulation that one of ordinary skill in the art would appreciate to provide heat retention within the crucible and prevent heat loss. Disposal body 20 includes thru-hole 28 disposed within a lateral wall thereof, with thru-hole 28 being in communication with internal cavity 26, such that waste gas 16 can flow from internal cavity 26 into first duct 30.

Crucible 10 includes crucible body 11 that forms crucible socket 12 and is configured to receive removable basket 4. Crucible 10 is formed from a material that is capable of being heated through induction. In an embodiment, crucible 10 is formed of 304 stainless steel. Heat is supplied to crucible 10 via one or more induction coils 14 that at least partially surrounds the outer surface of crucible 10. Induction coil 14 may be formed of any geometric shape, such as a hairpin, round, rectangular, spherical-helical, internal, or any other shape that one of ordinary skill in the art would appreciate heating crucible 10, such that waste 6 is vaporized within removable basket 4.

Removable basket 4 is configured to receive a predetermined amount of waste 6. In an embodiment, waste 6 may be placed directly in crucible 10. Removable basket 4 includes a plurality of apertures 8 configured to allow for even heat distribution within the crucible 10 during a heating cycle, which will be discussed in greater detail below. Apertures 8 may be formed as one or more geometric shapes arranged in a randomized or ordered pattern. Removable basket 4 is received within crucible socket 12, with basket 4 having a complementary geometric shape that is similar to that of the geometric shape of the crucible socket 12, thereby ensuring that the heat is transferred efficiently from crucible 10 to basket 4.

First duct 30 is disposed of through thru-hole 28 of waste disposal chamber 18, forming an airtight seal. First duct 30 couples catalytic converter 32 with waste disposal chamber 18, such that a fluid can be disposed through thru-hole 28 from internal cavity 26 to catalytic converter 32. In an embodiment, the fluid is waste gas 16. Catalytic converter 32 has a honeycomb metal structure that incorporates palladium, rhodium, and platinum into its surface. These metals convert the poisonous carbon monoxide and unburned hydrocarbons into non-toxic carbon dioxide and water vapor. In an embodiment, catalytic converter 32 is approximately 93 mm in diameter and 50 mm in height; however, the dimensions of catalytic converter 32 can be altered to accommodate for larger or smaller capacity waste destruction devices 2. Catalytic converter 32 may also incorporate copper, nickel, cerium, iron, manganese, or other metals known in the art to convert toxic compounds in waste gas 16 to less toxic and/or non-toxic compounds.

Figure 2:
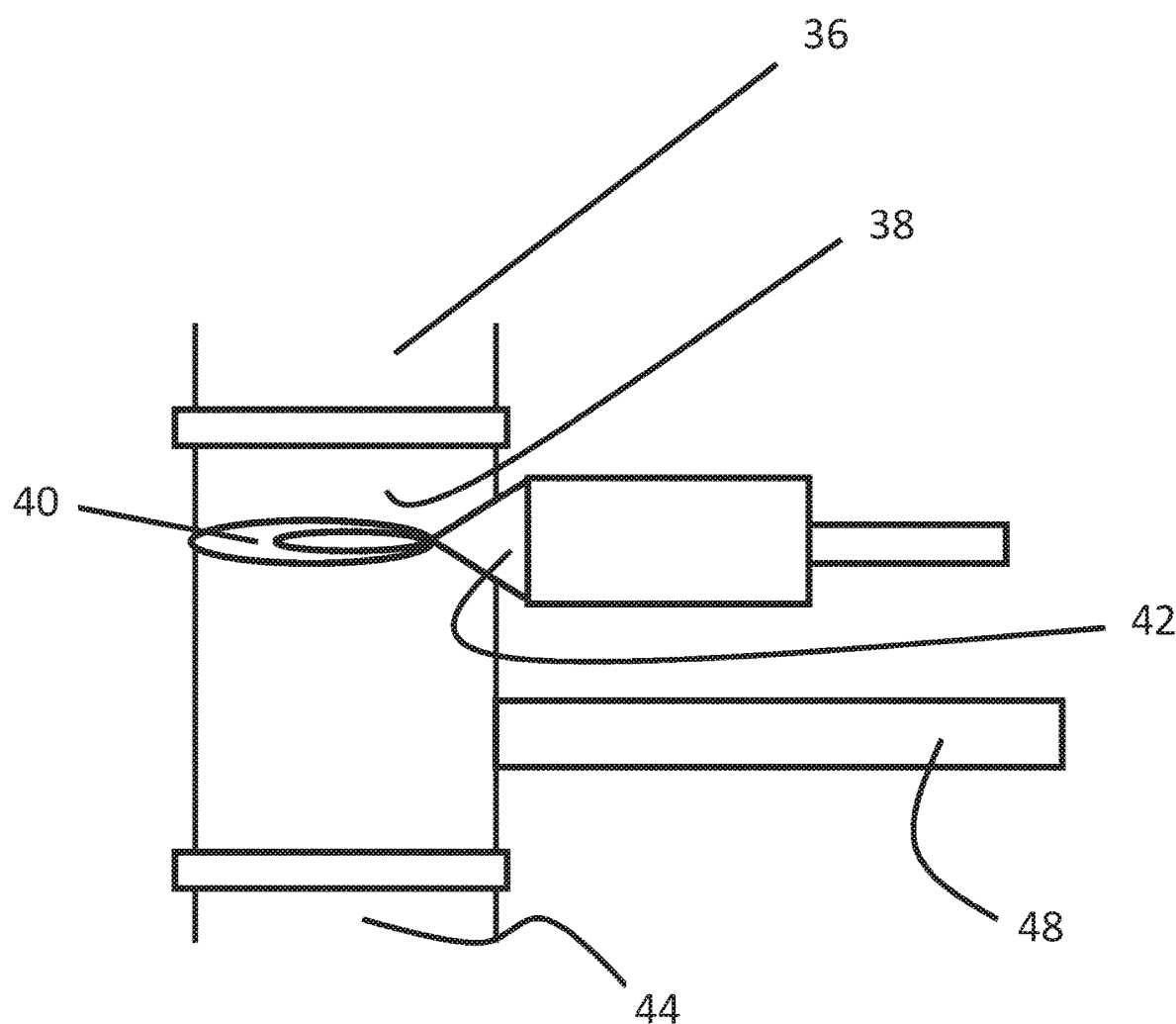
FIG. 2 is a perspective view of the plasma chamber of the waste destruction device.
Figure 3:
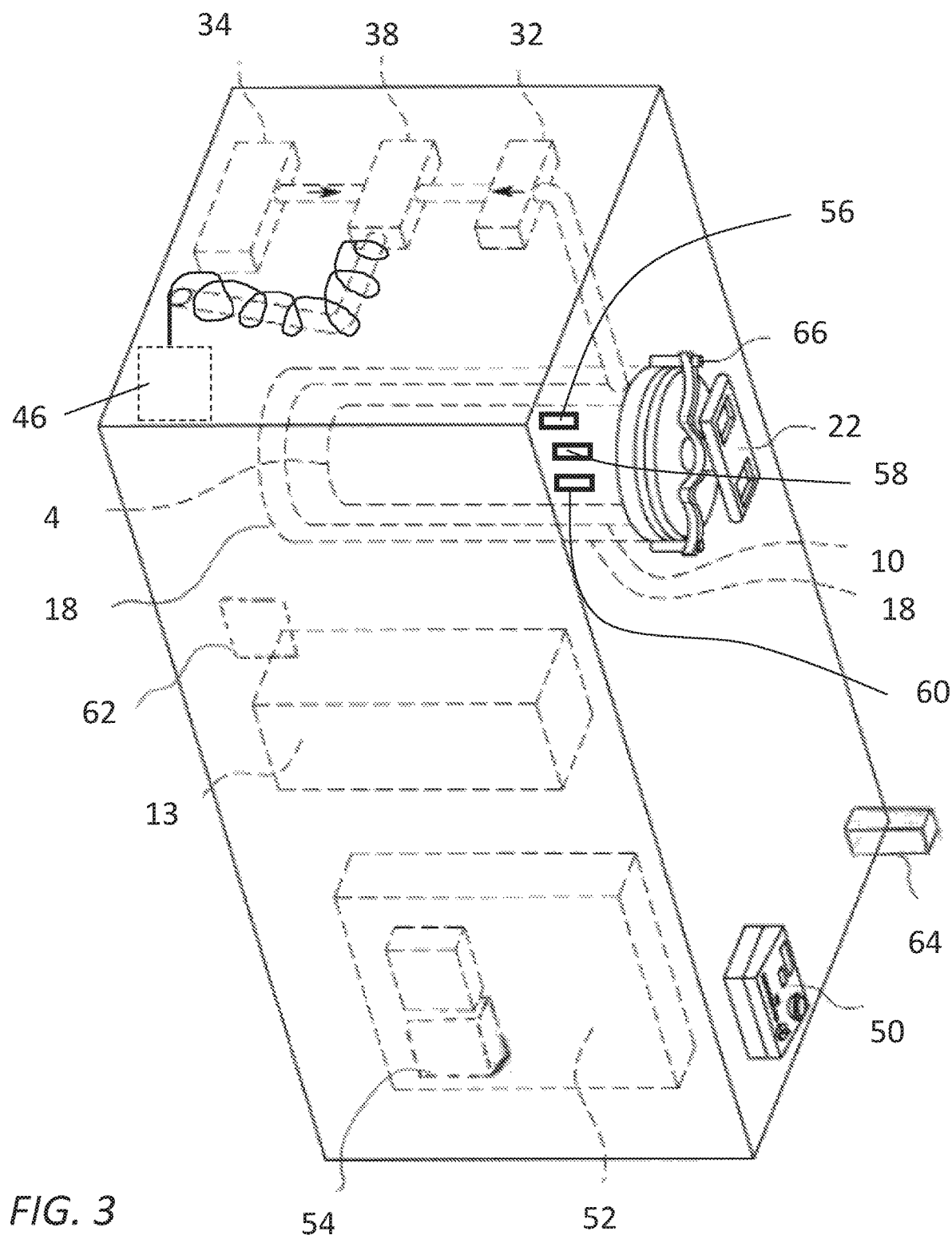
FIG. 3 is a perspective sectional view of the waste destruction device.

Second duct 36 couples catalytic converter 32 to plasma chamber 38, allowing a fluid to flow therebetween. As depicted in FIG. 2, plasma chamber 38 includes plasma head 42 that supplies the accelerated jet of hot plasma 40 within plasma chamber 38. Third duct 48 is coupled to plasma chamber 38 and allows for a fluid to flow between plasma chamber 38 and pressure altering pump 34, which is shown in FIGS. 1 and 3. Discharge duct 44 exhausts waste gas 16 from plasma chamber 38 to an environment surrounding waste destruction device 2. In an embodiment, first duct 30 couples directly with plasma chamber 38 such that a catalytic converter is not needed. Additionally, when first duct 30 couples directly to plasma chamber 38, third duct 48 may be referred to as the second duct.

Further referring to FIG. 1, third duct 48 includes a first end coupled to plasma chamber 38 and a second opposite end connected to pressure altering pump 34. In an embodiment, pressure altering pump 34 is an oil-less diaphragm vacuum pump and compressor. In an embodiment, pressure altering pump is a compressor, a vacuum pump, or a pump having both compressor and vacuum functions. Pressuring altering pump 34 creates a pressure differential to draw waste gas 16 through the components discussed herein. This pressure differential is the main driving force for the movement of waste gas within the system during the heating cycle. Pressure altering pump 34 also supplies compressed air within the waste destruction device during a cool-down cycle to rapidly cool the crucible and other components discussed above. Pressure altering pump 34 supplies the vacuum and may also force compressed air into waste disposal chamber 18 and over crucible 10 to provide a cooling effect during the cool-down phase of the waste destruction device 2, rapidly cooling down crucible 10. In an embodiment, pressure altering pump 34 may be housed within plasma chamber 38, such that third duct 48 is not needed.

As discussed above, crucible 10 is received within waste disposal chamber 18. To create a closed system and provide for low or zero oxygen environment within waste disposal chamber 18, removable lid 22 is in mechanical communication with coupling structure 24, sealing crucible 10 within waste disposal chamber 18 when removable lid 22 is secured, thereby creating an airtight seal. Oxygen is removed from the internal environment within waste disposal chamber 18 via pressure altering pump 34.

During a heating cycle, one or more induction coils 14 functions to heat crucible 10, providing a rapid increase in temperature within crucible 10. In an embodiment, induction coil 14 increases in temperature to between approximately 950° F. and 1400° F. Power to induction coil 14 is supplied by induction coil power supply 13. This rapid increase in temperature in the absence of oxygen results in the formation of waste gas 16 and a small amount of biochar residing in the bottom of removable basket 4, which may be dumped out after the cooling cycle. In an embodiment, waste gas 16 further includes a syn gas that results from the atomizing and ionizing of waste 6. Syn gas is a fuel gas mixture that primarily consists of hydrogen, carbon monoxide, and carbon dioxide and is burned off within plasma chamber 38, as discussed in further detail in FIG. 2. In an embodiment, waste gas 16 includes dioxins.

The vacuum provided by pressure altering pump 34 is maintained during the heating cycle such that waste gas 16 flows from waste disposal chamber 18 through first duct 30 to catalytic converter 32. Waste gas 16 then travels from catalytic converter 32 via vacuum pressure through second duct 36 and into plasma chamber 38. In plasma chamber 38 waste gas 16 passes through an accelerated jet of hot plasma 40, which incinerates any toxic dioxins and burning off sys gas within waste gas 16. Once waste gas 16 passes through hot plasma 40, waste gas 16 is exhausted through discharge duct 44 and exits waste destruction device 2 to an environment surrounding the waste destruction device 2. In an embodiment, as shown in FIG. 3, waste gas 16 flows through discharge duct 44 where heat exchanger 46 rapidly condenses the waste gas 16 into non-toxic compounds, such as carbon dioxide and water vapor.

FIG. 3 illustrates an embodiment of device 2 having user interface device 50 that is disposed to receive user input. User interface device 50, maybe a control panel. Upon receiving user input, user interface device 50 sends an electrical signal to programmable logic controller 52. Programmable logic controller 52 is in electronic communication with user interface device 50 and microprocessor 54. Microprocessor 54 receives the electrical signal and instructions from programmable logic controller 52 and sends/receives various electrical signals from temperature sensor 56, humidity sensor 58, oxygen sensor 60, carbon dioxide sensor 62, and induction coil power supply 13. Depending on electrical signals received from sensors 56, 58, 60, and 62, programmable logic controller 52 can shut down the system, increase the heat within crucible 10, or any number of control measures programmed on programmable logic controller 52.

Lid 22 may also include safety switch 66 having a first position and a second position, wherein the first position allows for operation of waste destruction device 2, and the second position prevents operation of waste destruction device 2. While FIG. 3 depicts safety switch 66 as being positioned on the lid, a person of ordinary skill in the art would appreciate any number of locations on waste destruction device 2 for which safety switch 66 could be positioned. For example, in an embodiment, safety switch 66 could be positioned within coupling structure 24 such that when removable lid is closed, safety switch 66 is automatically transitioned to first position and when removable lid 22 is opened, safety switch 66 is automatically transitioned into second position preventing operation of waste destruction device 2. In addition, FIG. 3 depicts status lights 64 disposed on a surface of device 2. Status lights 64 may be controlled by programmable logic controller 52 and are used to provide a visual indicator to a user to the current operational status of waste destruction device 2 (for example, a green light may signify that device 2 is on, a red light may signify that device 2 is off, and a yellow light may signify that device 2 is in an error state).

Figure 4:
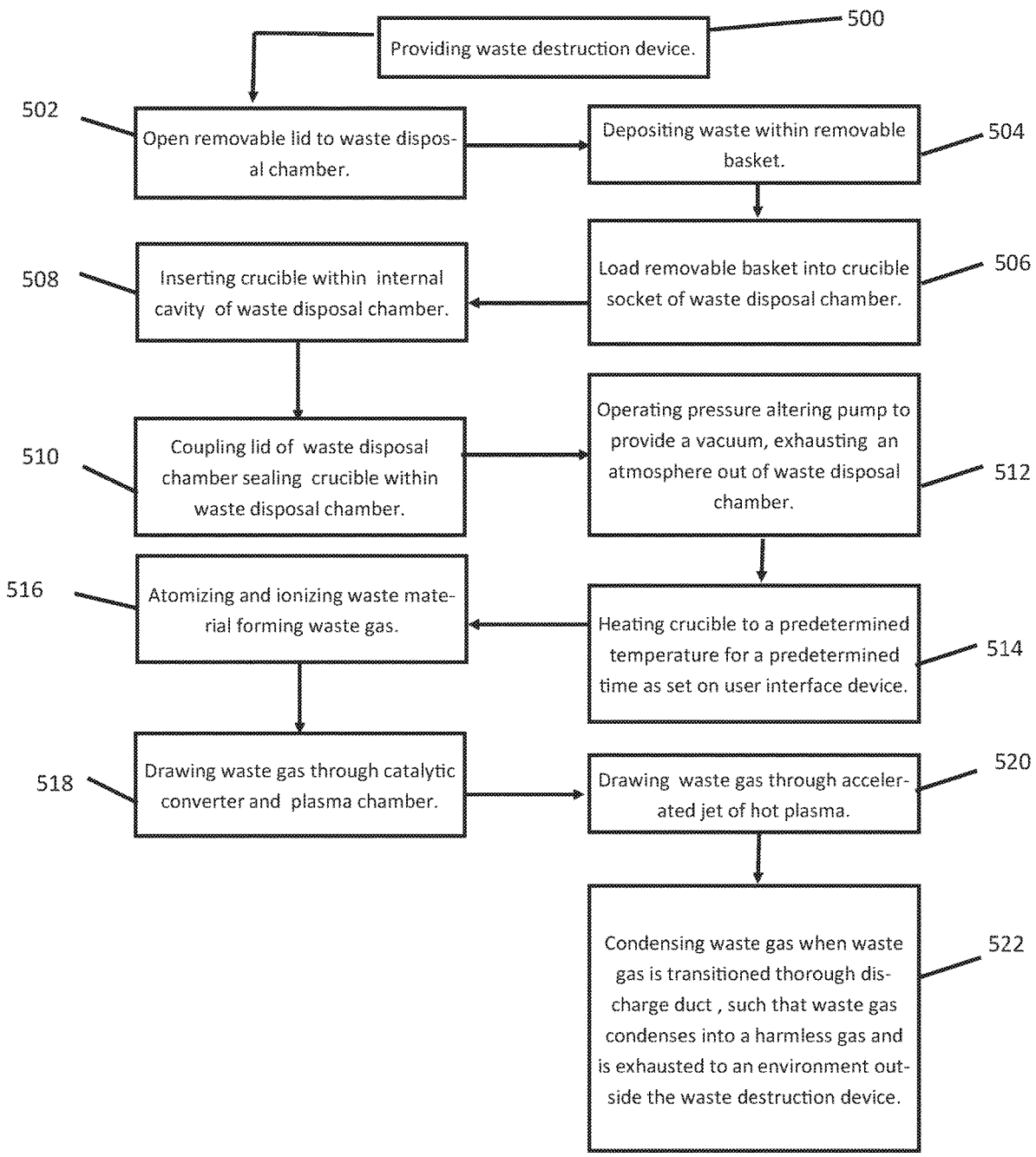
FIG. 4 is a flow chart diagram of a method for the destruction of biohazardous medical waste.

Referring now to FIG. 4, in conjunction with FIGS. 1-3, an exemplary process flow diagram is provided, depicting a method for the destruction of biohazardous medical waste. The steps delineated in the exemplary process flow diagram of FIG. 4 are merely exemplary of a preferred order of for the destruction of biohazardous medical waste. The steps may be carried out in another order, with or without additional steps included therein. Additionally, the steps may be carried out with an alternative embodiment of waste destruction device 2, as contemplated in the description above.

The method for the destruction of biohazardous medical waste begins at step 500, during which waste destruction device 2 is provided. Waste destruction device 2 includes the components discussed above. The method then proceeds to step 502, in which removable lid 22 is opened, exposing waste disposal chamber 18. In step 504, waste material 6 is deposited within removable basket 4. Step 506 details loading removable basket 4 into crucible socket 12 of waste disposal chamber 18. In step 508, crucible 10 is disposed within internal cavity 26 of waste disposal chamber 18. In step 510, lid 22 is coupled to waste disposal chamber 18 sealing crucible 10 therein. In step 512, pressure altering pump 34 is operated exhausting an atmosphere out of waste disposal chamber 18. In step 514, crucible 10 is heated to a predetermined temperature for a predetermined time as set on user interface device 50. In step 516, waste material 6 is atomized and ionized, forming waste gas 16. In step 518, waste gas 16 is drawn through catalytic converter 32 and plasma chamber 38. In step 520, waste gas 16 is drawn through plasma chamber 38, and passes over the accelerated jet of hot plasma 40. In step 522, waste gas 16 is condensed within discharge duct 44 and condenses into a harmless gas and is exhausted to an outside environment outside the waste destruction device 2.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A device for the destruction of waste comprising:
   a removable basket disposed to receive a predetermined amount of waste;
   a crucible configured to receive the removable basket, wherein an induction coil heats the removable basket, thereby atomizing and ionizing the waste disposed within the removable basket into a waste gas;
   a waste disposal chamber including an internal cavity configured to receive the crucible, the waste disposal chamber in fluidic communication with a plasma chamber via a duct, such that the waste gas flows from the waste disposal chamber to the plasma chamber; and
   the plasma chamber comprising a plasma head disposed within the plasma chamber, wherein the plasma head provides an accelerated jet of thermal plasma, such that when the waste gas flows from the waste disposal chamber and into the plasma chamber, the waste gas passes over the accelerated jet of hot plasma thereby incinerating dioxins within the waste gas, wherein the waste gas is discharged into an environment surrounding the device.

2. The device of claim 1, wherein the device further includes a catalytic converter disposed between the waste disposal chamber and the plasma chamber, such that waste gas flowing from the waste disposal chamber to the plasma chamber flows through the catalytic converter.

3. The device of claim 1, wherein device further includes a second duct having a first end and a second opposite end, wherein the first end is connected to the plasma chamber and the second end is connected to a pressure altering pump.

4. The device of claim 1, wherein a discharge duct extends away from the plasma head, such that the waste gas flows to the external environment via the discharge duct once the waste gas passes over the accelerated jet of hot plasma, wherein the discharge duct further includes a heat exchanger configured to cool the gas within the discharge duct rapidly.

5. The device of claim 1, further including a safety switch having a first position and a second position, wherein the first position allows for operation of the device and the second position prevents operation of the device until the safety switch is transitioned into the first position.

6. The device of claim 1, further including a control panel, wherein the control comprises:
   a user interface device, wherein the user interface device is disposed to receive a user input;
   a programmable logic controller, wherein the programmable logic controller includes a microprocessor such that when the user input from the user interface device is received by the programmable logic controller, the programmable logic controller operates a microprocessor to send an electrical signal to the group consisting of a temperature sensor, a humidity sensor, a carbon dioxide sensor, and an oxygen sensor.

7. The device of claim 1, wherein the device further includes a carbon dioxide sensor for detecting the carbon dioxide levels within the environment that surrounds the device.

8. The device of claim 1, wherein the crucible further includes a humidity sensor, wherein based on a determination that the induction coils have been operating for greater than 60 minutes and the humidity exceeds 80%, the device shuts down.

9. The device of claim 1, wherein the crucible further includes a temperature sensor, wherein the temperature sensor monitors the internal temperature of the crucible to ensure that the internal temperature is within a predetermined temperature range.

10. The device of claim 9, wherein the predetermined temperature range is between 950° F. and 1400° F.

11. The device of claim 1, wherein the crucible further includes safety gas sensor, wherein when a sufficient level of oxygen is detected within the crucible, the device is shut down to prevent a flare-up within the crucible.

12. The device of claim 1, wherein the removable basket further includes a plurality of apertures, to ensure an even distribution of heat within the crucible.

13. The device of claim 1, wherein a high-temperature insulation resides between the crucible and the enclosure body, preventing heat loss within the crucible.

14. The device of claim 1, further including a visual indicator displaying the operating status of the device.

15. A device for the destruction of waste comprising:
   a crucible configured to receive a predetermined amount of waste, wherein an induction coil is in thermodynamic communication with the crucible, such that the induction coil heats the waste, thereby atomizing and ionizing the waste disposed within the crucible into a waste gas;
   a waste disposal chamber defining an internal cavity configured to receive the crucible;
   a first duct having a first end and a second opposite end, wherein the first end is in fluidic communication with the internal cavity and the second end is coupled to a plasma chamber, such that the waste gas flows from the catalytic converter to the plasma chamber via the first duct;
   the plasma chamber comprising:
      a plasma head disposed within the plasma chamber, wherein the plasma head provides an accelerated jet of thermal plasma; and
      a discharge duct extending away from the plasma head, wherein when the waste gas flows from the second duct into the plasma chamber it passes over the accelerated jet of thermal plasma, such that dioxins within the waste gas are incinerated and having the waste gas flow through the discharge duct and into an environment surrounding the device; and
   a second duct having a first end and a second opposite end, wherein the first end is connected to the plasma chamber, and the second end is connected to a pressure altering pump.

* * * * *